United States Patent [19]

Dietrich

[11] 3,963,441

[45] June 15, 1976

[54] ARTICLE WITH A LYOPHILIZED IMMUNOREACTIVE SELF-ADHERING COATING

[75] Inventor: Rolf Dietrich, Neu-Aesch, Switzerland

[73] Assignee: Hoffmann-La Roche Inc., Nutley, N.J.

[22] Filed: Nov. 18, 1974

[21] Appl. No.: 524,430

[30] Foreign Application Priority Data

Dec. 10, 1973 Switzerland.................. 17272/73

[52] U.S. Cl. ........................ 23/253 R; 23/230 B; 23/253 TP; 424/12; 424/88; 424/89; 424/92; 195/103.5 R
[51] Int. Cl.² .......................................... G01N 33/16
[58] Field of Search ............... 23/230 B, 253 R; 424/12; 195/103.5 R

[56] References Cited
UNITED STATES PATENTS

| | | | |
|---|---|---|---|
| 3,378,481 | 4/1968 | Saravis | 23/230 B |
| 3,389,966 | 6/1968 | Saravis | 23/230 B |
| 3,843,324 | 10/1974 | Edelman | 424/12 |

Primary Examiner—Morris O. Wolk
Assistant Examiner—Sidney Marantz
Attorney, Agent, or Firm—Samuel L. Welt; George M. Gould

[57] ABSTRACT

An article for carrying out immunologic determinations. The article is provided with a lyophilized immunologic-reactive coating which is self-adhering to a carrier. The article is useful in diagnosing various diseases.

15 Claims, No Drawings

ARTICLE WITH A LYOPHILIZED IMMUNOREACTIVE SELF-ADHERING COATING

BACKGROUND OF THE INVENTION

Diagnostic procedures in humans and animals are making use of immunological principles to an increasing extent. These reactions are used to detect antibodies or antigens in the body fluids of the organism. An antigen is an extraneous substance which, when applied to the organism, activates the formation of certain soluble or cellular substances denoted as antibodies. Any substance, such as for example a protein, which is not normally present in a certain organism, can cause the formation of antibodies when it infiltrates into or is applied to an organism under suitable conditions.

The antibodies formed can react in vitro and in vivo with the antigens, whereby they can carry out a protective function in the case of an infection.

Immunological test procedures are based on this antigen-antibody reaction, the presence of an antigen or an antibody being confirmed or determined by bringing the appropriate antibody or the appropriate antigen into contact with a body fluid of the organism, mainly blood serum, blood plasma, urine or a specially treated blood extract. However, other body fluids can also be used. In the presence of the appropriate antibody or antigen in the body liquid of the organism, there is formed an antigen-antibody complex which is visible, for example, by color change, precipitation or agglutination, or which can be determined by radioactivity or fluorescence measurement.

In such procedures, the often sensitive, immunologically reactive materials have to be stored and applied to a carrier. Thus, for example, suspensions of these materials can be used, but these suspensions suffer from the disadvantage that they have a limited stability and must be applied on to the carrier which is expensive for the user. Such suspensions have to be stored, namely in a refrigerator, in use have to be applied on to the carrier using a micropipette or an inoculation loop and have to be subsequently dried. When lyophilized suspensions are used, the stability is substantially improved. but the disadvantage of the time-consuming application on to the carrier is not overcome.

In order to eliminate this latter disadvantage, an attempt has been made to provide the user with a carrier having already dried streaks of an immunologically reactive material. These carriers have the advantage that they are ready-for-use after simple thawing of the streaks. However, such carriers have to be stored at −20°C since otherwise the stability is extremely slight.

In accordance with the present invention, there has been found a process which makes it possible to apply immunologically reactive materials in a lyophilized and self-adhering form to a carrier, the advantages of the lyopholized suspension with respect to stability being combined with the advantages of the dried streaks with respect to simplified and time-saving preparation and handling.

More particularly, the present invention is concerned in one of its aspects with a process for applying an immunologically reactive material on to a carrier in a self-adhering and lyophilized form, wherein a suspension of the immunologically reactive material is applied to the carrier, allowed to dry and subsequently lyophilized.

Further, in another of its aspects, the present invention is concerned with a carrier for immunological determinations, said carrier containing immunologically reactive material in a lyophilized and self-adhering form.

The expression "immunologically reactive materials" relates to materials as, for example, proteins, peptides, polysaccharides, etc which are of decisive significance for an immunological determination, i.e., the presence of these materials is the determining factor in the immunological test procedure. These materials can be detected in the body fluids of humans and animals using immunological principles or can serve for their detection.

Especially suitable immunologically reactive materials are pathogenic and facultatively pathogenic organisms such as, for example, parasites, protozoa, bacteria or viruses or their immunologically active components, isolated antibodies from humans and animals, serum constituents, toxins, hormones, enzymes, alkaloids, cell and tissue extracts, substances with a small molecular weight such as, for example, insulin, angiotensin and urokinase, biogenic amines, blood cells, particles chemically or physically covered with antigens or antibodies, such as, for example, erythrocytes or latex particles.

Particularly suitable immunologically reactive materials for use in the present invention are *Toxoplasma gondii*, *Trypanosoma cruzi* and *Entamoeba histolytica*.

All types of carriers are suitable in accordance with the present invention; for example, object carriers, films, etc which are used in the medicinal field or in laboratories. The carriers can consist of any suitable material such as, for example, glass or a synthetic material and are advantageously transparent. Especially preferred carriers are object carriers having at least one depression for receiving the immunologically reactive material.

In a preferred embodiment, the carrier is an object carrier which has corresponding depressions on both the top and bottom surfaces. The depressions on the top surface serve to receive the immunologically reactive material, while the depressions on the bottom surface serve to protect the surface from mechanical damage such as, for example, scratches, which impair the optical properties. The object carrier advantageously has a writing area at one end.

The object carrier of the preferred embodiment contains several depressions and accordingly enables the qualitative examination of several sera or the quantitative examination of several serial dilutions of a serum. In addition, this object carrier is suitable for the application of several different immunologically reactive materials and accordingly for the simultaneous determination of various antigens or antibodies in a test sample.

In accordance with the process provided by the present invention, the immunologically reactive material is suspended in a suitable liquid, applied to the carrier, dried and lyophilized.

Especially suitable as the suspension liquid is an aqueous solution such as, for example, a saccharose or sodium chloride solution. The method of application is not critical, but the suspension is preferably applied dropwise to the carrier. The drying temperature depends on the composition of the applied suspension and the sensitivity of the reagents. However, the drying is advantageously carried out at a temperature between 0°C and 100°C, preferably between 20°C and 40°C. The drying time depends on the sedimentation rate of the suspended material and the temperature, but it usually amounts to at least 5 minutes. The lyophilization is carried out in the usual manner in a conventional freeze dryer. The coated carrier manufactured in this manner can be stored at temperatures above 0°C and accordingly does not require freeze preservation.

The present invention can be used in any diagnostic method where an immunologically reactive material is applied to a carrier in a lyophilized form. However, the carrier in accordance with the present invention is advantageously used in the form of an object carrier with lyophilized antigens in an immunofluorescence method. An indirect immunofluorescence method is especially preferred.

For the specific detection of antibodies which are formed in the human or animal organism against exogenous substances (infection defence) or endogenous substances (autoagression), the indirect immunofluorescence method has, in fact, proved to be especially good. In such a method, in the first step an object carrier having applied antigens is contacted with the corresponding body fluid, incubated and subsequently washed. In this manner, a gammaglobulin (antibody) modified according to the antigen can react with the antigen and accordingly remain attached to the object carrier. When such antibodies are present in the sample under examination, in a second step their binding to the antigen is detected with antihuman-globulin which is provided with a fluorescent coloring material. For this purpose, the marked antihuman-globulin is added to the object carrier which is subsequently incubated and rinsed. The marked antihuman-globulin reacts with the modified gammaglobulin (antibody) which is bound to the antigen, such that the fluorescent coloring material remains attached to the object carrier and the corresponding fluorescence can be detected microscopically. The existence of a fluorescence signifies that antibodies which correspond to the antigens applied to the carrier are present in the sample under examination and thus enables the diagnosis of diseases which are related with such antibodies or antigens.

The following Table provides a selection of typical diseases or conditions which can be determined with the aid of the carrier in accordance with the invention according to the immunologically reactive materials lyophilized on to the carrier.

Table

| Antigen | Disease |
| --- | --- |
| Toxoplasma gondii | Toxoplasmosis |
| Entamoeba histolytica | Amoebiasis |
| Trypanosoma cruzi | Chagas |
| Trypanosoma gambiense/rhodesiense | Sleeping sickness |
| Leishmania donovani | Leishmaniasis |
| Schistosoma mansoni | Schistosomiasis |
| Echinococcus granulosus | Echinococcosis |
| Filariae | Filariasis |
| Fasciola hepatica | Fascioliasis |
| Plasmodia | Malaria |
| Candida species | Candidiasis |
| Aspergilli | Aspergillosis |
| Mycropolyspora faeni/Micromonospora vulgaris | Farmer's lung |
| Treponema pallidum | Syphilis |
| Neisseria gonorrhoeae | Gonorrhea |
| Neisseria meningitis | Meningitis |
| Brucella abortus | Brucellosis |
| Mycoplasma pneumoniae | Pneumonia |
| Australia antigen | Acute hepatitis |
| Herpes simplex virus | Herpes simplex |
| Influenza virus | Flu |
| Cell nuclei | Systemic lupus erythematosis or Scleroderma |
| Cryptococci | Cryptococcosis |
| Torulopsis species | Systemic mycosis |

The following Examples illustrate the present invention:

EXAMPLE 1

0.03 ml of a suspension of *Toxoplasma gondii* (6 million/ml) in a 2.5 percent aqueous solution of saccharose is added dropwise to each depression of a 1 mm thick polystyrene object carrier (76 mm × 26 mm) having eight numbered depressions (diameter 6 mm, depth 0.25 mm) on the top surface and corresponding depressions on the bottom surfaces, as well as a writing area. (The Toxoplasmae were prepared according to A. Betz, Bull. World Hlth. Org. 39, 1968 p. 367–374). The object carrier coated in this manner is incubated at 37°C for 30 minutes in a drying cupboard with air circulation. Subsequently, the suspension is frozen on to the object carrier using dry ice and then lyophilized in a freeze dryer. There is obtained a ready-for-use object carrier having self-adhering Toxoplasmae which are not detached upon rinsing with water.

EXAMPLE 2

0.03 ml of a suspension of *Entamoeba histolytica* (5,000/ml) in a physiological 0.85 percent sodium chloride solution with 2 percent Cabowax is added dropwise to each depression of a 1 mm thick polystyrene object carrier (76 mm × 26 mm) having eight numbered depressions (diameter 6 mm, depth 0.25 mm) on the top surface and corresponding depressions on the bottom surface, as well as a writing area. (The amoebae were prepared according to Morris Goldman, American J. Trop. Med. Hyg. Vol 15 No. 5, 1966 p. 694–700). The object carrier coated in this manner is incubated at 37°C for 30 minutes in a drying cupboard with air circulation. Subsequently, the suspension is frozen on to the object carrier using dry ice and then lyophilized in a freeze dryer. There is obtained a ready-for-use object carrier having self-adhering amoebae which are not detached upon rinsing with water.

EXAMPLE 3

A serial dilution of a patient's serum is prepared (1/50, 1/100, 1/200, 1/400, 1/800, 1/1600, 1/3200 and 1/6400). One drop of each of the diluted serum is applied by means of a pipette to each depression of the object carrier prepared as described in Example 1. The object carrier is then incubated for 0.5 hour at 37°C in a moist chamber and subsequently washed with a buffered sodium chloride solution (pH 7.2). One drop of a commercially available suspension of antihuman-globulin marked with fluorescein isothiocyanate is applied to each depression using a pipette. The object carrier is then incubated for 0.5 hour at 37°C in a moist chamber and subsequently washed with a buffered sodium chloride solution (pH 7.2). The object carrier is then rinsed with distilled water and dried with a filter paper. One drop of a commercially available immersion oil is added to each depression and the fluorescence is determined by means of an immersion objective in a fluorescence microscope. The maximum dilution in which the fluorescence can still be determined gives an indication of the relative concentration of the Toxoplasma antibodies.

EXAMPLE 4

Serum samples from eight different patients are each diluted 5-fold with a buffered sodium chloride solution (pH 7.2) and numbered from 1 to 8. One drop of each of these numbered, diluted serum sample is applied by means of a pipette to each of the depressions, numbered from 1 to 8, on the object carrier prepared according to Example 1. The object carrier is incubated for 0.5 hour at 37°C in a moist chamber and subsequently washed with a buffered sodium chloride solution (pH 7.2). One drop of a commercially available suspension of antihuman-globulin marked with fluorescein isothiocyanate is applied to each depression using a pipette. The object carrier is then incubated for 0.5 hour at 37°C in a moist chamber and subsequently washed with a buffered sodium chloride solution (pH 7.2). The object carrier is then rinsed with distilled water and dried with a filter paper. One drop of a commercially available immersion oil is added to each depression and the fluorescence is determined by means of an immersion objective in a fluorescence microscope. Those depressions in which a fluorescence is determined correspond to serum samples of patients who have been infected with Toxoplasmae.

EXAMPLE 5

A serial dilution of a patient's serum was prepared (1/50, 1/100, 1/200, 1/400, 1/800, 1/600, 1/3200 and 1/6400). One drop of each of the diluted serum is applied by means of a pipette to each depression of the object carrier prepared according to Example 2. The object carrier is then incubated for 0.5 hour at 37°C in a moist chamber and subsequently washed with a buffered sodium chloride solution (pH 7.2). One drop of a commercially available suspension of antihuman-globulin marked with fluorescein isothiocyanate is applied using a pipette to each depression. The object carrier is then incubated for 0.5 hour at 37°C in a moist chamber and subsequently washed with a buffered sodium chloride solution (pH 7.2). The object carrier is then rinsed with distilled water and dried with a filter paper. One drop of a commercially available immersion oil is added to each depression and the fluorescence is determined by means of an immersion objective in a fluorescence microscope. The maximum dilution in which the fluorescence can still be determined gives an indication of the relative concentration of the *Entamoeba histolytica* antibodies.

EXAMPLE 6

Serum samples of eight different patients are each diluted five-fold with a buffered sodium chloride soluton (pH 7.2) and numbered from 1 to 8. One drop of each of these numbered, diluted serum samples is applied by means of a pipette to each of the depressions, numbered from 1 to 8, on the object carrier prepared as described in Example 2. The object carrier is then incubated for 0.5 hour at 37°C in a moist chamber and subsequently washed with a buffered sodium chloride solution (pH 7.2). One drop of a commercially available suspension of antihuman-globulin marked with fluorescein isothiocyanate is applied by means of a pipette to each depression. The object carrier is then incubated for 0.5 hour at 37°C in a moist chamber and subsequently washed with a buffered sodium chloride solution (pH 7.2). The object carrier is then rinsed with distilled water and dried with a filter paper. One drop of a commercially available immersion oil is added to each depression and the fluorescence is determined using an immersion objective in a fluorescence microscope. Those depressions in which a fluorescence is determined correspond to serum samples of patients who have been infected with amoebae.

EXAMPLE 7

0.3 ml of a suspension of *Trypanosoma cruzi* (2 million/ml) in a 2.5 per cent aqueous solution of saccharose is added dropwise to each depression of a 1 mm thick polystyrene object carrier (76 mm × 26 mm) having eight numbered depressions (diameter 6 mm, depth 0.25 mm) on the top surface and corresponding depressions on the bottom surface, as well as a inviting area. (The Trypanosomae were prepared according to Allain D. S. and Kayan G., The Journal of Parasitology, Vol 60, No. 1 February 1974 pages 179–184). The object carrier coated in this manner is incubated at 37°C for 30 minutes in a drying cupboard with air circulation. Subsequently, the suspension is frozen on to the object carrier using dry ice and then lyophilized in a freeze dryer. There is obtained a ready-for-use object carrier with self-adhering trypanosomae which are not detached upon rinsing with water.

EXAMPLE 8

A serial dilution of a patient's serum is prepared (1/50, 1/100, 1/200, 1/400, 1/800, 1/1600, 1/3200 and 1/6400). One drop of each of the diluted serum is applied by means of a pipette to each depression of the object carrier prepared as described in Example 7. The object carrier is then incubated for 0.5 hour at 37°C in a moist chamber and subsequently washed with a buffered sodium chloride solution (pH 7.2). One drop of a commercially available suspension of antihuman-globulin marked with fluorescein isothiocyanate is applied to each depression by means of a pipette. The object carrier is then incubated for 0.5 hour at 37°C in a moist chamber and subsequently washed with a buffered sodium chloride solution (pH 7.2). The object carrier is then rinsed with distilled water and dried with a filter paper. One drop of a commercially available immersion oil is added to each depression and the fluorescence is determined by means of an immersion objective in a fuorescence microscope. The maximum dilution in which the fluorescence can still be determined gives an indication of the relative concentration of the *Trypanosoma cruzi* antibodies.

EXAMPLE 9

Serum samples of eight different patients are each diluted five-fold with a buffered sodium chloride solution (pH 7.2) and numbered from 1 to 8. One drop of each of these numbered, diluted serum sample is applied by means of a pipette to each of the depressions, numbered from 1 to 8, on the object carrier prepared as described in Example 7. The object carrier is incubated for 0.5 hour at 37°C in a moist chamber and subsequently washed with a buffered sodium chloride solution (pH 7.2). One drop of a commercially available suspension of antihuman-globulin marked with fluorescein isothiocyanate is applied by means of a pipette to each depression. The object carrier is then incubated for 0.5 hour at 37°C in a moist chamber and subsequently washed with a buffered sodium chloride solution (pH 7.2). The object carrier is then rinsed with distilled water and dried with a filter paper. One drop of a commercially available immersion oil is added to each depression and the fluorescence is determined by means of an immersion objective in a fluorescenc microscope. Those depressions in which a fluorescence is determined correspond to serum samples of patients who have been infected with *Trypanosoma cruzi*.

I claim:

1. An article useful for immunological determinations which article comprises a carrier material having at least part of one surface thereof physically coated with an immunological reactive material which is provided in stable and self-adhering form in the absence of a bonding reagent by applying a suspension of said immunological reactive material to said carrier material, drying and then lyophilizing.

2. The article of claim 1 wherein said carrier material is in the form of an object carrier.

3. The article of claim 2 wherein said object carrier has a top surface having one or more depressions, said immunologically reactive material being coated within said depressions.

4. The article of claim 3 wherein said object carrier also has one or more depressions on its bottom surface.

5. The article of claim 1 wherein said immunologically reactive material comprises antigens.

6. The article of claim 1 wherein said immunologically reactive material comprises antibodies.

7. The article of claim 1 wherein said immunologically reactive material comprises proteins.

8. The article of claim 1 wherein said immunologically reactive material comprises peptides.

9. The article of claim 1 wherein said immunologically reactive material comprises polysaccharides.

10. The article of claim 1 wherein said immunologically reactive material comprises Toxoplasmae.

11. The article of claim 1 wherein said immunologically reactive material comprises amoebae.

12. The article of claim 1 wherein said immunologically reactive material comprises Trypanosomae.

13. A method for preparing articles useful for immunological determinations which method comprises applying a suspension of an immunologically reactive material to at least one surface of said article, allowng said article to dry and then lyophilizng said article so as to provide said immunologically reactive material as a partial coating on said surface of said article in lyophilized and self-adhering form.

14. The method of claim 13 wherein sodium chloride solution is used for said suspension.

15. The method of claim 13 wherein said article is dried at a temperature between 20°C. and 40°C.

* * * * *